(12) United States Patent
Robert et al.

(10) Patent No.: US 7,965,385 B2
(45) Date of Patent: Jun. 21, 2011

(54) INSTALLATION FOR CANDLING EGGS AND OPTOELECTRONIC SYSTEM FOR EXAMINING UNDER RADIATION SUCH AN INSTALLATION

(75) Inventors: Pierre Robert, Cholet (FR); Olivier Somville, Cholet (FR)

(73) Assignee: Visio Nerf S.A. (FR)

( * ) Notice: Subject to any disclaimer, the term of this patent is extended or adjusted under 35 U.S.C. 154(b) by 49 days.

(21) Appl. No.: 12/208,386

(22) Filed: Sep. 11, 2008

(65) Prior Publication Data

US 2009/0201323 A1    Aug. 13, 2009

Related U.S. Application Data

(63) Continuation of application No. PCT/FR2006/002895, filed on Dec. 22, 2006.

(30) Foreign Application Priority Data

Dec. 23, 2005 (FR) .................................. 05 13252
Jan. 3, 2006 (FR) .................................. 06 00018

(51) Int. Cl.
*A01K 43/00* (2006.01)
*G01N 33/08* (2006.01)

(52) U.S. Cl. .............................................. 356/52

(58) Field of Classification Search .................. None
See application file for complete search history.

(56) References Cited

U.S. PATENT DOCUMENTS

| 2,167,853 | A | * | 8/1939 | Roberts ........................ 356/54 |
| 3,540,824 | A | | 11/1970 | Fonda et al. |
| 4,063,822 | A | * | 12/1977 | deJong et al. ............... 356/408 |
| 4,805,778 | A | | 2/1989 | Nambu |
| 4,843,958 | A | | 7/1989 | Egosi |
| 5,017,003 | A | | 5/1991 | Keromnes et al. |
| 5,898,488 | A | | 4/1999 | Kuhl |
| 5,900,929 | A | | 5/1999 | Hebrank et al. |

(Continued)

FOREIGN PATENT DOCUMENTS

DE     20213117 U1 *  3/2003

(Continued)

OTHER PUBLICATIONS

PCT/FR2006/002895, International Search Report, May 10, 2007, 3 pages.

*Primary Examiner* — Tarifur Chowdhury
*Assistant Examiner* — Gordon J Stock, Jr.
(74) *Attorney, Agent, or Firm* — St. Onge Steward Johnston & Reens, LLC

(57) ABSTRACT

The invention relates to a system applicable to an installation for candling eggs, to determine the presence of fertilized eggs in the cells of the egg crate grid moving on a conveyor. Row by row, the analyzing device synchronously monitors the light emission on the eggs of the row and detection of the attenuated light of emerging beams. The monitoring includes at least two close cycles of light emission. During the first cycle, which is of short duration to avoid causing glare of the detectors of the detecting device, the coordinates of possible empty cells in a row are determined and stored. During the second cycle, which is of longer duration, the coordinates of fertilized eggs of the row are determined and stored. The egg candling installation advantageously also marks the eggs, depending in particular on whether they are fertilized or not.

10 Claims, 2 Drawing Sheets

U.S. PATENT DOCUMENTS 6,427,844 B2 * 8/2002 Hebrank .................. 209/510
7,333,187 B2 * 2/2008 Hebrank .................. 356/53

FOREIGN PATENT DOCUMENTS

| | | |
|---|---|---|
| EP | 1457108 A2 | 9/2004 |
| FR | 1285525 | 7/1962 |
| FR | 2768517 | 3/1999 |
| JP | 9127096 | 5/1997 |
| WO | 9914589 | 3/1999 |
| WO | 0036411 | 6/2000 |
| WO | 0156789 | 8/2001 |

* cited by examiner

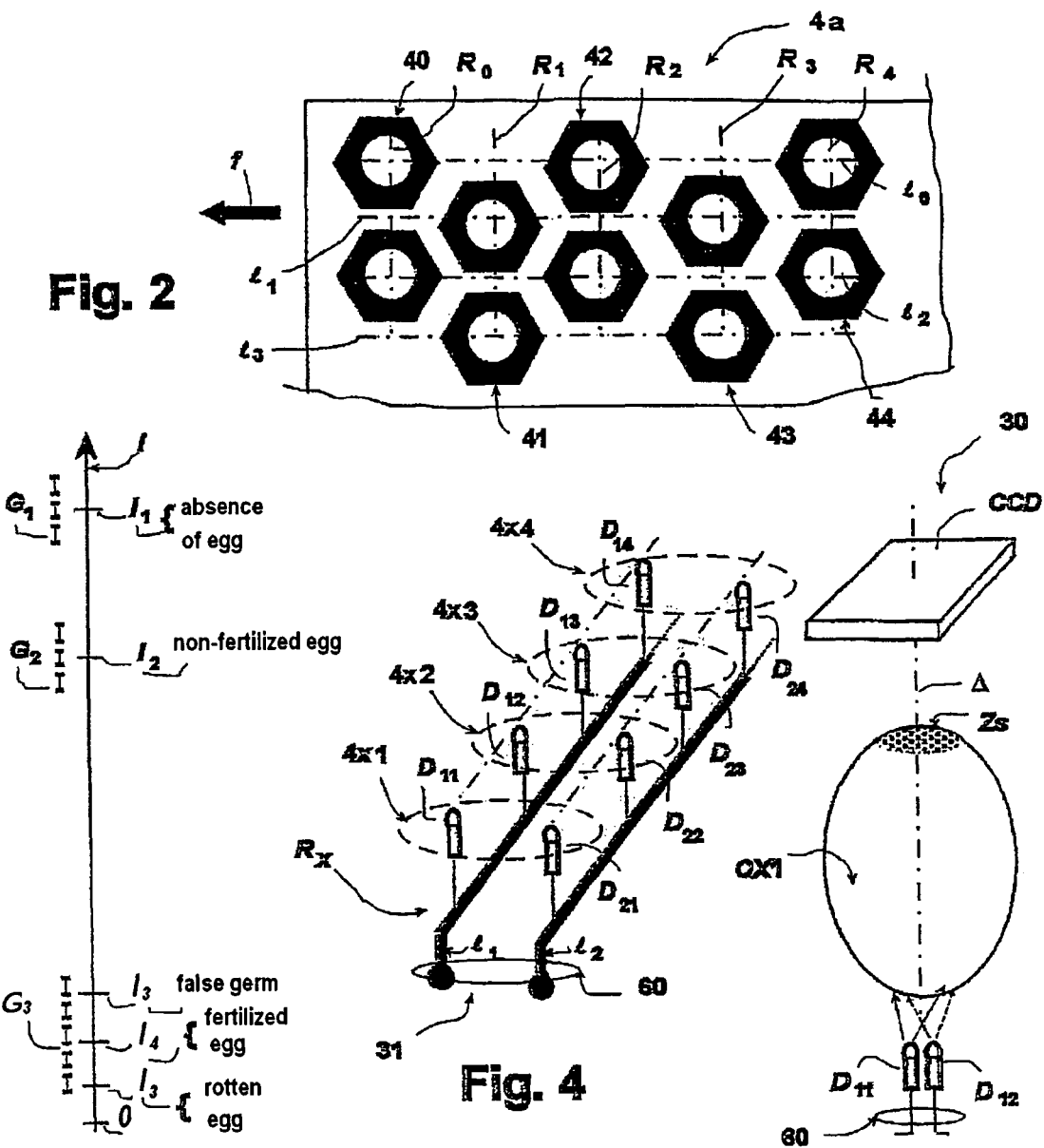

US 7,965,385 B2

INSTALLATION FOR CANDLING EGGS AND OPTOELECTRONIC SYSTEM FOR EXAMINING UNDER RADIATION SUCH AN INSTALLATION

CROSS-REFERENCE TO RELATED APPLICATIONS

The present application is a continuation of pending International patent application PCT/FR2006/002895 filed on Dec. 22, 2006 which designates the United States and claims priority from French patent application 0513252 filed on Dec. 23, 2005 and 0600018 filed on Jan. 3, 2006, the content of which is incorporated herein by reference.

FIELD OF THE INVENTION

The invention relates to techniques for visiometric examination applied to objects arranged for examination in defined discrete locations and in successive rows, in a continuous series following a regular spatial distribution that is repeated periodically. The concept of visiometric examination is taken here as including all techniques of the optoelectronic type that involve the capture of an image that detects a light beam coming from each object submitted to examination under incident rays, as well as an analysis by image processing on the received signals, controlled by adapted software, in order to deduce the condition of the examined objects in terms of established characteristics. In addition, the concept of object, in the context of this invention, covers what will appear later as an absence of object. In other words, the objects to be considered are instead considered locations, since it is understood that these locations correspond to the aforementioned relative arrangement that is periodically repeated in successive rows.

BACKGROUND OF THE INVENTION

In the following text, various applications of the invention are described, with more specific reference to its preferred applications in the field of the food industry for candling eggs. The locations subjected to radiation examination in this case are, in practice, the various cells of the egg crate grid in which the eggs are arranged, each being held in one of the cells. In addition, the egg candling operations, as they are currently practiced at an intermediate stage in the production of chicks for chicken eggs, between an incubator and a hatching device, are intended to examine the eggs by transparency by submitting them individually to a light beam, usually of infrared light, in order to establish a distinction between the eggs based on the state of fertilization of each, and thus to allow selection of those that have been fertilized while excluding those that have not been fertilized, with the fertilized eggs being sent to the hatching devices where the chicks are born. Specifically, each egg is characterized as fertilized or non-fertilized according to the diminution in a light beam to which it is exposed. However, whether this is done for eggs, for any other type of product in individualized units, or even for discrete locations made up of adjacent zones of a contained product, it will obviously be possible for the professional to transpose the vocabulary to apply the invention to other criteria of discrimination and selection, as well as other industrial areas.

In conventional egg candling installations, including those described in particular in patent application WO 99/14589 (Ecmas) or in the American U.S. Pat. No. 5,900,929 (Embrex), the practice is to process the egg crate grids in series, each grid containing a batch of eggs. Generally, direct use is made of crate grids used for incubating eggs. Eggs are placed therein in cells arranged in locations at regular intervals, in each egg crate grid, following a repeated pattern of longitudinal lines and latitudinal rows. The grids are placed successively horizontally over a conveyor appliance (for instance, of the conveyor belt type that rotates in a closed circuit), which conveys them through the optoelectronic examination site.

In this site, a radiating source emits an incident light flow that illuminates each of the eggs individually. When dealing with an application aimed at locating the air chamber inside the eggs, these means of illumination for the eggs are arranged on the same side as the detectors that receive the light emerging from the eggs and determine its composition according to the modification caused by each of them. The same would be true if, for instance, the application consisted in examining the coloring of fruits that were individually maintained, instead of eggs, in the cells of similar crate grids. However, in the more common application, i.e. egg candling, aimed at distinguishing fertilized eggs from those that are to be removed from the particular series, as in our example here, the source is generally placed below the conveyor circuit of the crate grids, to produce illumination from below to above toward the detecting appliances located above. It is advantageous but not obligatory to use a light that lies within the range of the infrared wavelength.

For detection methods that are sensitive to the emerging flow, one can use either individual sensors that are associated with each egg respectively, or preferably a video camera. When the detected light intensity descends below a predetermined threshold, indicating an attenuation threshold that can be computed in known manner depending on the diffusion properties of the eggs or determined experimentally, indicating the presence of an embryonic germ, and the system is instructed to automatically designate the examined eggs as being fertilized. The cell structure of the incubation crate grids is naturally adapted to optical examination. In general, the cells are bottomless, for examination by transmission, and they maintain the eggs with the large vertical axis, which lends itself well to an examination that is advantageously produced in the vicinity of this large axis.

The locations in lines and rows, especially for the cells that receive eggs, are most commonly configured with square patterns, or triangular, or particularly hexagonal patterns, in the style known as quincunx. Quincunx arrangements differ from those in square patterns in that, from one row to the next, the cells are no longer aligned in the longitudinal moving direction, but are offset laterally. For instance, if the offset distance can be any fraction of the pace of distribution of the cells within each row, the most frequent quincunx arrangement corresponds to a displacement of a half-step in a regular distribution of the hexagonal type.

In addition, the means of illumination and the associated means of detection are arranged and controlled to match the spatial configuration of the cells of the crates. In industrial applications, an optimal compromise between cadence of the processing, reliability of the sorting, costs of installation and operation requires simultaneous operation on a group of locations of eggs in repetitive manner in the course of the passage through a visiometric examination point in which the material remains stable. This means that in general, the examination takes place row by row as the successive rows pass under the detectors. From this point of view, the invention foresees, as will be explained further hereafter, examination of the displaced rows of the quincunx arrangements by considering them grouped together in order to use the same means of illumination and means of detection, for instance on the even numbered row and the odd numbered row in each pair of rows of a hexagonal arrangement.

In a preferential manner, the analysis by visiometric analysis aimed at detecting the presence of fertilized eggs takes place at the entry to the egg-candling installation. The crates are placed manually or automatically on the conveyor device, for instance a conveyor on a rotating belt in closed circuit, which takes them through the visiometric examination site. On leaving said site, the installation is advantageously supplemented by a marking station, where the eggs are marked selectively so that they are transferred thereafter toward distinct reserved destinations, depending on whether they are fertilized or not. The sorting is generally carried out manually to eliminate from the chain the non-fertilized eggs, but it can also be performed automatically by a supplementary apparatus.

The invention aims to improve the conditions for industrial exploitation of such egg-candling installations, principally concerning the reliability of the detection of the state of fertilization of the eggs and the cadence of processing. Especially in the case of an installation in which the egg crates are treated linearly in a marking station after the visiometric examination station, the problem arises of being able to mark the eggs efficiently and rapidly by directly utilizing the signal produced by numerical processing of the images captured by the visiometric examination while taking care not to risk breaking the egg shells. In the same concern for processing at high cadence in full security in the selection of the eggs depending on their state of fertilization, it is useful to find a solution to difficulties that appear at the visiometric examination station where more than two conditions are to be distinguished for each location of the entire group that is passing through, especially if in some rows of eggs certain cells have remained empty accidentally.

SUMMARY OF THE INVENTION

Considering one of these aspects, the present invention takes note of the fact that the means of attenuation of the light beams can be strongly disturbed by phenomena of reflection of the sensors of the video camera when the luminous flows that must be detected at one and the same instant are at levels of intensity too different and for this reason lead to false information concerning the condition of the eggs examined. This situation arises frequently, for example in the presence of a rotten egg or of an empty cell among the clear, fertilized eggs. It is clear here that the absence of egg in a cell, allowing passage of the entire luminous flow, is indicated by an illumination of very great intensity, much higher than when an egg is present there, no matter what its condition may be. At the same time, when the egg present in a particular cell is a clear egg, it attenuates the luminous flow passing through it very little, but the attenuation of this flow is noticeably stronger for an egg with false seed, a fertilized egg, a rotten egg, these three cases being cited here in the order of the growing attenuations.

As a non-restricting example, the diagram in FIG. 3, appended to this description, schematically illustrates the sale of luminous intensities/captured by the detection video camera. The intensities include three very distinct ranges of luminous intensity:

$G_1$: very high illumination corresponding to the case "absence of egg" (intensity $I_1$);

$G_2$: high illumination corresponding to the case "clear egg" (intensity $I_2$);

$G_3$: weak illuminations corresponding to cases "false germ" (intensity $I_3$), "fertilized egg" (intensity $I_4$), and "rotten egg" (intensity $I_5$).

In view of the presence of this very wide range of luminous intensities, there is the risk of "glaring" of the video camera sensor. In fact, modern apparatuses most often use a monolithic sensor with semiconductors of the "CCD" type (meaning "Charge Coupled Device"). This type of sensor can consist of a chain of photo detector or photo site elements. These photo detectors convert the captured light into electric signals. They in turn are aligned on the chain parallel to the rows of cells and they function simultaneously for all the cells of each row passing through the visiometric examination site. If the photon flow striking one of the photo detectors is excessively energetic, the aforementioned glaring phenomenon appears, as can be seen from a parasitic diffusion of electrons toward the neighboring photo detector elements. The most disturbing result in the chick production industry can be, for instance, that the absence of an egg in one cell falsifies the result for neighboring cells and that for each of these cells, even if an egg is present, it is impossible to distinguish whether it is fertilized or not. In other words, this condition can cause a dysfunction of the processing series of the signals (processing carried out by the automatic analysis apparatus), and eventually may result in preventing correct differentiation between conditions of transparency presented by eggs in cells belonging to the same row as the cell that caused the error and which are examined at the same time.

In the current state of the art, it is thus necessary to discard all the eggs in this row, which naturally causes waste and financial losses that should be avoided. In the case of an industrial application, it is not thinkable to stop the detection procedure, since the sorting goes on at a very fast rate or cadence, typically on the order of 6,000 eggs per hour.

It could seem sufficient to contract or attenuate the scale of luminous intensities to avoid this phenomenon, while attenuating the maximum level of luminous intensity (absence of egg: intensity $I_1$). However, it has been observed that the range $G_3$ is made up of levels of luminous intensity that are relatively close to one another. This can make it difficult to discriminate between the three levels of this range. To obtain a good contrast and to be capable of making this discrimination, it is necessary to resort to a relatively strong illumination dosage, which causes an expansion of the range $G_3$, but also correlatively over the complete range of intensities and thus the maximum illumination level, causing increased risk of glare. In a more general case, it is possible to encounter any number of ranges of levels of luminous intensity that are quite far apart from one another. And as in the case of egg candling, the ranges of sensitivity of the examination by luminous radiation are often closer to a range of the logarithmic type that to a proportional range.

It therefore becomes necessary to be able to avoid risks of glare for the detection sensor, while preserving the possibility of fine discriminations between light intensities at levels relatively close to one another, that is, to avoid a strong contrast, which seems completely contradictory.

The invention aims to overcome the disadvantages of apparatuses known in the art. It therefore proposes to conduct the visiometric examination of each row in successive stages (at least two), illuminating the batches for examination by illumination doses that are set differently from one stage to the other between two successive stages, and in a second stage illuminating only those batches that, in a first stage, were not shown to present a condition that would cause glaring of the sensor in the second stage.

In particular, the invention takes the form, in terms of procedure, of an analytical process of objects contained in batches based on a repetitive distribution of longitudinal lines and transversal row on a conveyor that passes them in a line in longitudinal direction through a visiometric examination site that includes sensor means sensitive to emergent light beams retransmitted by the said objects, characterized in that the examination of each row is conducted in at least two stages or cycles of successive actions, illuminating the batches for examination by different doses of illumination and in a second stage illuminating only those batches that, in a preceding first stage, were not shown to present a condition that would cause, in a second stage, a glaring of the sensor means which could disturb the neighboring batches in the same row during the examination.

Considering the preferred fields of application of the invention, which present situations identical or similar to those of egg candling, that is, in which it is the intention to determine a condition to be attributed to each of the said objects on the basis of consequences they cause in a light beam to which they are exposed during the passage from each of the successive rows of a batch of eggs that are to be sorted on the basis of being clear or fertilized, or similar objects contained in cells of a crate grid forming said batches, there are certain secondary characteristics of the invention, which apply individually or simultaneously in any technically operative combination; these advantageous characteristics are as follows:

The two successive measurement cycles are advantageously conducted, respectively, in the course of a principal second stage carried out under conditions appropriate for determining a condition of transparency or similar condition affecting the decrease in the light beam in a noticeable manner for the sensor of the emergent beam, which is preceded by a first stage conducted under conditions appropriate for revealing the presence of empty cells and determining and recording the coordinates of their batches in the row being examined, in order to control the illumination conditions during the second stage to avoid illuminating them.

In addition, the radiation dose selected for the sensitivity range of each stage is advantageously regulated by varying the time of exposure at a determined emitting power. Because the radiation dose is selected for each stage to avoid risk of glare of the neighboring sensors around a batch without egg (or similar object), it can easily be seen that the duration of the objects' exposure, for each row, is relatively brief for the first stage and relatively long for the second stage.

The light source illuminating the objects to be examined is advantageously made up of a series of light-emitting diodes, or LED. These diodes or LED are arranged parallel to the rows of the batches to be analyzed, and thus in a direction perpendicular to the displacement of the objects moved by the conveyor. More precisely, they are aligned parallel to the rows of cells in the crate grid that receive the eggs, thus generally following a row perpendicular to the longitudinal direction of conveyance.

According to a secondary characteristic of the invention, the different illumination doses are applied during at least two successive cycles, sufficiently close together in time to illuminate the same row that is under way in the visiometric examination post, said cycles utilizing the same diode sources, at the same intensity, but for different durations, in order to accommodate at least two different ranges of sensitivity, while avoiding between one and the other the glare phenomenon in some or all of the photo detectors.

During the first measurement cycle, a relatively weak dose is applied and the automatic analysis apparatus detects the presence or absence of empty cells, and if any are found, it determines and stores their coordinates in the examined row (the ordinal number in the transversal position in this row). During the second measurement cycle, with a relatively strong dose the illumination of the only cell batches that are not empty are controlled. The automatic analysis apparatus discriminates, if they exist, those cells that contain clear eggs as opposed to those containing other categories of egg, particularly fertilized eggs, and it records the respective coordinates of these two potential categories of cells. These coordinates are particularly simple to express by the ordinal number of the cell in the row and the ordinal number of this row in the longitudinal line in the crate grid.

The luminous doses—respectively, relatively weak and relatively strong—are selected such that the second allows a contrast of the level of the photo detectors, to distinguish fertilized from non-fertilized eggs, and the first reveals the batches where the application of the second would involve for corresponding photo detectors the presence of too high a luminous intensity, which might cause a glare phenomenon.

Further characteristics of the invention concern the organization of spatial arrangements correlated to the photo detectors of the video camera and the diodes of illumination, where the activation of these two series of elements are synchronized by automatic control devices.

Thus, in the case where the cells present a quincunx configuration, it is advantageous to group the rows of cells two by two, providing a light source made up of a number of LED that is twice the number of cells per row. In this configuration, each diode is activated in correspondence with the passage in its field of one row of cells out of two. In other words, in this configuration, half of the diodes are associated with even-numbered lines of cells, and the other half with odd-numbered lines.

It is also possible to increase the number of illumination cycles, so that each cycle involves a different illumination dose (especially for a duration that is appropriate for a light intensity that remains identical), for instance, to use three cycles. During the third cycle, in the preferred application of the invention concerning egg candling, the automatic analysis apparatus distinguishes the eggs that are truly fertilized from other categories of non-clear eggs (eggs with false germ, rotten egg). Only the cells that can contain one or the other of these categories of non-clear eggs (following the analysis conducted during the second measurement cycle) are illuminated during the third cycle.

Following these successive discriminations, the eggs can be sorted and/or marked upon leaving the candling installation. In practice, and in a preferred embodiment, it is the clear eggs that are marked and/or sorted, and then eliminated, so that only fertilized eggs are preserved. In general, it is sufficient therefore to proceed in two stages, under working conditions determined so as not to illuminate empty cells during the second stage of illumination that allows detection of the presence of clear, non-fertilized eggs, considering that it is not important if among the correctly fertilized eggs there remain some eggs with false germ or even rotten eggs, neither of which could lead to the birth of a chick.

It can also be useful, however, to conduct a more thorough analysis by working in more than two stages. In particular, the invention makes it possible to draw up useful statistics by recording the results in computerized databases and submitting them to specially adapted computations to determine such data as the profitability of fertilization or the quality of a delivery received in a hatchery.

Concerning an apparatus, the invention particularly involves a system of optoelectronic analysis that applies preferably to an installation for candling eggs contained in crate grid cells that are adapted to showing at least two conditions, fertilized and clear respectively, such that said cells are arranged in batches based on a predetermined configuration of lines and rows.

Said installation includes, in a known manner, a conveyance apparatus that moves successive egg crate grids at a predetermined speed through a visiometric examination site that comprises a light source generating a light beam appropriate for each of said eggs in each successive row passing through said site, and means of synchronized detection of the emergent beams from said eggs, as well as means for automatically determining a condition of said eggs, particularly a fertilized or non-fertilized condition, on the basis of the attenuation caused by each egg in the corresponding beam.

In the various types of application of the invention that are best adapted to industrial practice, the light source is provided by a number of light-emitting diodes aligned parallel to the rows of batches receiving eggs in the crate grids (the cells), and the means of detection takes the form of a sensor made up of a chain of a number of photo-detectors sensitive to emitted light, the spatial configuration of which is correlated with that of said light-emitting diodes. Appropriate means are then foreseen to synchronously guide, first, the selective emission of beams by said light-emitting diodes in such a way as to simultaneously illuminate predetermined cells in each row passing through the examination site and, second, the reception of the emergent beams by photo-detectors of said sensor in spatial relation with the light-emitting diodes emitting light.

According to the invention such guidance is programmed to automatically ensure at least two measurement cycles of the decrease by light emission of predetermined duration delivering different doses of illuminations, each avoiding a glare of the detection means sensitive to emergent beams, namely a first cycle during which the emitted light illuminates all cells of the row under examination during the first duration, in order to determine the existence or non-existence of cells without an egg, taking the form of the detection of a non-attenuated light at high energy, and to register in the memory the coordinates of the batches according to whether the corresponding cells are void of an egg or not, and a second cycle during which the emitted light illuminates only the cells whose coordinates indicate that an egg is present, while a second duration, longer than said first duration, in order to discriminate fertilized eggs from clear eggs, by detection of different decreases in the light emerging from said eggs. For further exploitation, possibly in a later site of the same installation, means are provided for recording in memory the coordinates of fertilized and/or clear eggs.

The invention is now described in greater detail with reference to the appended drawings.

BRIEF DESCRIPTION OF THE DRAWINGS

FIG. 2 shows schematically a preferred embodiment for a carton grid for transporting eggs to be examined, which are inserted into the installation of FIG. 1, shown in partial overhead view.

FIG. 3 shows schematically a scale of luminous intensities of emergent beams for various categories of eggs when they are illuminated by an infrared light source.

FIG. 4 shows schematically a configuration of LED light source applied in the automatic detection and analysis system of FIG. 1.

FIG. 5 shows a detail of an egg and the detection by a sensor of light retransmitted from said egg.

DETAILED DESCRIPTION OF THE INVENTION

Figure 1:
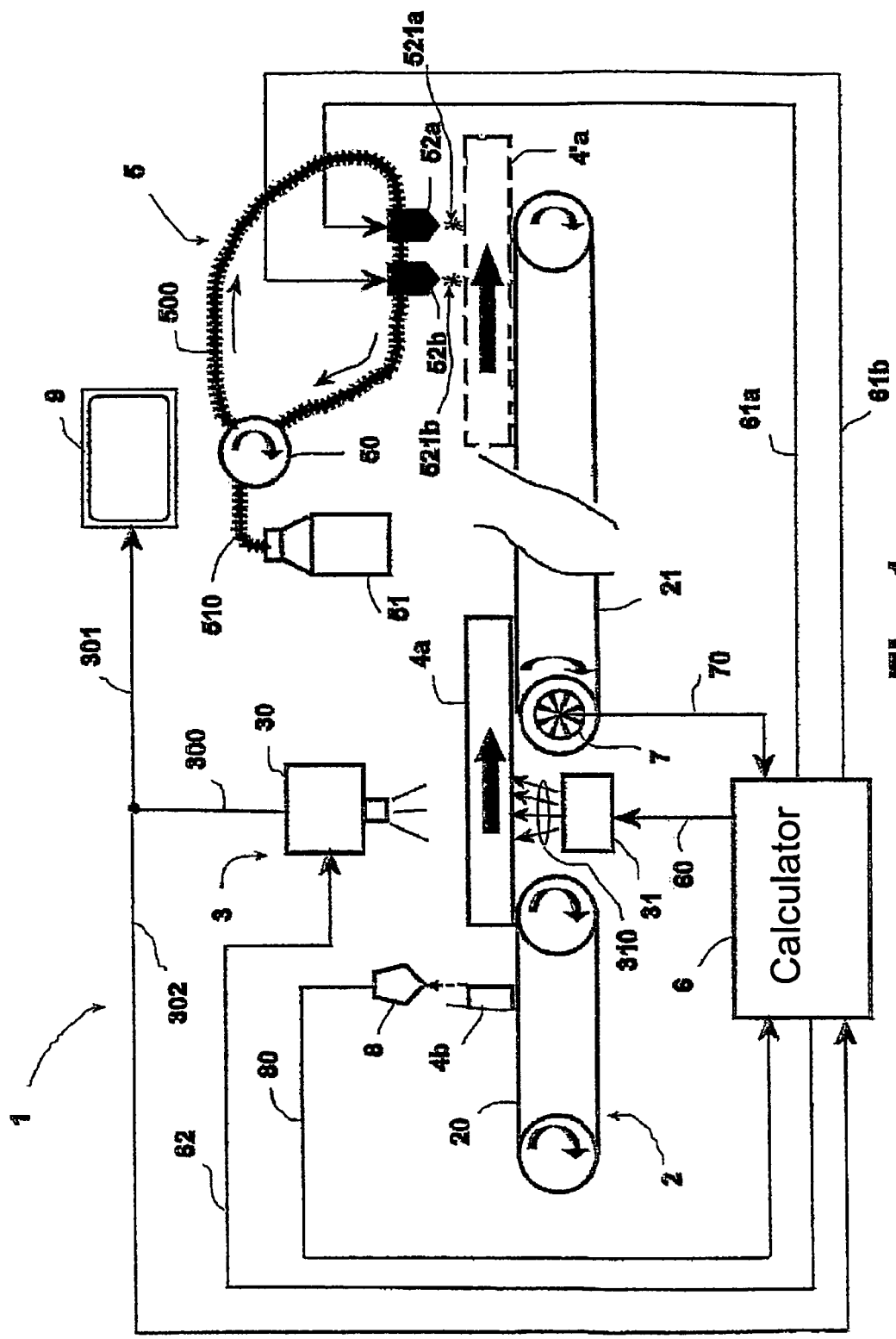
FIG. 1 shows schematically an example according to the invention of an installation for candling eggs incorporating a visiometric examination site as well as a marking site for non-fertilized eggs.

Before describing, with reference to FIG. 1, the functioning of the optoelectronic system that includes an automatic detection apparatus and an analysis apparatus for fertilized eggs in the strict sense, we describe here an example of the layout of an egg-candling installation 1 incorporating such a system, according to a preferred embodiment of the invention. In the figures that follow the common elements bear the same reference numbers and are re-described only as necessary.

With the exception of advantageous characteristics specific to the invention, which will be pointed out in detail below, the general layout of such an installation in for the most part basically common to those installations known in the art. Reference is made to the French patent 2 768 517, for instance. It is an additional advantage of the system of the invention that permits re-utilization of well-known technologies and of material that is financially amortized.

Thus the installation 1 comprises a conveyor 2 with rotating belt in closed circuit or equivalent apparatus, present in the illustrated example an entry area 20 and an exit area 21. This conveyor displaces through the visiometric examination site, generally at fixed speed, carton grids containing eggs to be candled (not shown), which are introduced one at a time, manually, at the entry to the installation. The carton grids are advantageously the same that were used for incubating the eggs.

A visiometric examination site 3 is stationary between the two portions of the conveyor 20 and 21. It comprises in the lower area a source of radiation 31, which in the particular case considered here emits individual beams of infrared light, and in the upper area means of detection which are sensitive to the wavelength of the light emitted by the source 31 and are made up of discrete detectors or, preferably, of a video camera 30. The source 31 as well as the sensor of the video camera 30 is described more completely hereafter, in terms of make-up and synchronized functioning, in relation to FIGS. 4 and 5.

Each of the crate grids of eggs introduced successively on the conveyor 2, for instance the crate grid 4a, breaks the beam 310 emitted by the source 31 between the two portions of the conveyor. It comprises a number of cells in which eggs are placed for candling. The structure of these cells is such that they allow the passage of the beam 310 in the absence of eggs (the bottom is generally open). The eggs contained in these cells intercept the beam 310 and retransmit it with variable decrease according to their condition, and particularly, in the context of the application described here, as a function of their fertilized state, that is, whether the egg is fertilized or not. This effect that is to be measured is not due, strictly speaking, to the transparent quality of the egg, but rather to the degree of diffusion of the light that penetrates the egg. This, in addition, is why the measurement implies that the illumination beam strikes the corresponding shell of the egg, even if it does not exactly follow its axis.

The radiation registered by the video camera 30 is converted into electric signals that are transmitted onto an outlet connection 300, advantageously in the form of numeric signals, first to a visualization element 9, for instance a cathode screen (connection 301), and also to a data processing system with recorded program 6 (connection 302), referred to hereafter simply as a calculator. The latter can be a dedicated signal processor or can be of a standard type and equipped with appropriate ports. The calculator, using image processing, controlled by specific software in known manner in the art, analyzes the signals of images received from the video camera 30. The image processing carried out in this manner makes it possible to determine whether the eggs analyzed are fertilized by situating the extent of attenuation in the light beam at the crossing of each egg in relation to threshold values that limit predetermined ranges.

In a variant embodiment of the described installation, the visualization element 9, which is optional, can be controlled by signals received from the calculator 6, and not directly from the video camera 30, that is, after processing of the signals.

A preferred application for egg crate grids according to a practical embodiment of the invention, the crate grid 4a for instance, is illustrated schematically in the detailed view in FIG. 2 (a partial overhead view). It shows a number of cells, referred to generally as 40 to 44, that are intended to receive eggs for candling (not expressly shown). These cells 40 to 44 are arranged in successive rows aligned parallel with respect to one another and perpendicular to the longitudinal direction of motion (arrow f). The illustration thus depicts five rows $R_0$ to $R_4$ by four lines $l_0$ to $l_3$ in the longitudinal direction, in an arrangement based on an orthonormal matrix. However, from one row to the next, the cells are in a quincunx arrangement. In an arrangement that is more precisely hexagonal, they are offset by a half-step in the transversal direction between the even-numbered rows and the odd-numbered rows.

The infrared source 31 (FIG. 1) is composed of a number of light-emitting diodes (LED). These diodes are arranged on a line parallel to the rows, $R_0$ to $R_4$, of the crate grids, for instance 4a; that is, following an orthogonal direction to their movement. They are at a distance to one another, by the value of a half-step in the particular case considered here, so that each one passes through the successive cells of the same line respectively, in the course of the relative motion. LED 31 are controlled in pulse mode by the calculator 6 (connection 60) at a rhythm determined according to the speed of the conveyor, and synchronized with the procession of the cells, so that each diode produces a basic illuminating beam of one cell at the moment it passes in front of the diode, and thus that said beam is modified by the egg it contains before being detected by the video camera 30 in order to be analyzed.

FIG. 4 schematically illustrates the configuration of the light source 31 of FIG. 1 which is composed of a number of LED, emitting in the infrared range. These diodes are arranged in a line parallel to the rows of crate grids, and thus to a row $R_x$ of the x order assumed to be undergoing examination, that is following a perpendicular direction orthogonal to the longitudinal direction of procession through the visiometric examination site.

In the particular case illustrated for a configuration of cells in quincunx pattern, the number of diodes, $D_{x1}$ to $D_{x4}$, is double that of the cells of one row. It is assumed that the row $R_x$ was of odd number and included cells 4×1 and 4×3 (assuming that there are four lines), symbolized by ellipses in dotted lines. The diodes have been labeled $D_{x1}$ to $D_{x4}$. In the described example, at the moment depicted in FIG. 4, only the diodes $D_{x1}$ and $D_{x3}$ are activated for the odd-numbered rows, because they are placed under the cells 4×1 and 4×3. When the following row of cells is above diodes, it is the diodes $D_{x2}$ and $D_{x4}$ that will be activated for this even-numbered row.

It is important, however, to emphasize that this arrangement is in no way restrictive for the conditions for applying the invention. Many situations exist in which it will instead be advantageous to produce the illumination by means of several groups of diodes, particularly two or three groups implanted beside one another. Thus the polyvalence of the machine is increased and it can easily be adapted to crate grids with different dimensions and steps. The illumination of the diodes is controlled selectively according to the arrangement of the cells in the crate grids. The selection of the diodes to be illuminated is functionally equivalent to the mechanical adjustment of the position of the diodes under the cells.

In all cases, each illuminated diode produces a basic beam intended to individually illuminate one of the cells of the row under examination in the visiometric site. The diodes as a whole are controlled in pulse mode by the calculator 6: multiple connection 60.

FIG. 5 schematically illustrates the illumination of an egg OX1, placed in cell 4×1 in the row $R_x$ by the diode $D_{x1}$.

The video camera 30 comprises a sensor labeled CCD as mentioned above. According to an important characteristic of the invention, the sensor CCD is controlled by the calculator 6 synchronously with the control of the diodes, $D_{x1}$ to $D_{x4}$. In addition, the linear spatial configuration of this sensor is correlated with that of these diodes. The control of the sensor CCD is provided by the generation of command signals on a connection 62 linking the calculator to a command input of the video camera 30.

Referring to the diagram of FIG. 3, the illumination with precaution for a cell without eggs runs the risk of causing a glade of photo-detectors of the sensor CCD which receives the light flow that has not undergone any attenuation. The captured light intensity I1 is in fact very high. To clarify, if the video camera being used tolerates an average current of 100 mA (after conversion of the luminous energy into electric signals), a luminous pulse causing a current of 1 A, if its duration is sufficient, will generate an average current exceeding the admitted limit of 100 mA. The glare phenomenon will thus be caused.

Thus, according to an important characteristic of the invention, it is likely that two measurement cycles will be applied to each row successively undergoing examination.

The first cycle consists in generating, under the command of the calculator (connection 60), a pulse of light illuminating each of all the cells in the row. The pulse command signals are transmitted to all diodes, $D_{11}$ to $D_{24}$. Continuing by way of example, the duration of this pulse is typically on the order of 100 µs, for the video camera characteristics indicated above.

The first measurement cycle makes it possible to detect the possible batches of cells that contain no egg. The calculator 6 authorizes the activation (command signal on the connection 62) of the photo-detectors of sensor CCD situated on the lines of cells of the row under examination, receives (connection 302) the electric signals emitted from the optoelectronic conversion carried out by this sensor, analyzes the image signals thus received, and subjects them to an automatic processing after which it orders the recording, in memory elements (not shown) that are associated with it, coordinates in the current crate grid of empty cells whose existence was detected, contrary to the cells in which an egg is present.

Then a second measurement cycle is activated. Altogether or in part, the diodes $D_{x1}$ to $D_{x4}$ receive a second command pulse generated by the calculator 6 to illuminate once again the eggs present in their cells, for instance egg OX1. The illumination is selective. Only the diodes that correspond spatially with the non-empty cells are activated. On the connection 60 the calculator 6 therefore transmits command signals only to these diodes, on the basis of analytic results obtained at the end of the preceding cycle and of the recorded coordinates that distinguish the empty and non-empty cells.

The pulse is of greater duration than that of the first pulse, so as to expose the eggs to a greater quantity of light, since use is made of identical light intensity. In synchronized manner, the calculator 6 sends a signal (connection 62) to the video camera authorizing the detection of the beams emitted by the activated diodes such as they are retransmitted attenuated by the eggs.

In another example, the duration of the pulse generated during the second cycle is typically of the order of 1 ms. This exposure time makes it possible to distinguish the clear eggs (FIG. 3: intensity $I_2$) from the other categories of eggs, the light intensities ($I_3$ to $I_5$) transmitted through eggs and received by the sensor CCD for these categories that are close to one another. This differentiation is effected by the calculator 6, which to this end receives the signals (connection 302) emitted by the optoelectronic conversion performed by the sensor.

Since the empty cells (if they exist) are not exposed, there is no further risk of glare of the photo-detectors, because the attenuation caused by the other categories of eggs, whatever it may be, is sufficiently strong.

For each row in the process of testing the two cycles follow one another at a sufficient rapid rate so that the axes of vertical symmetry Delta (FIG. 5) of the illuminated eggs do not have time to move significantly in terms of the test conditions, given the speed of motion that is imposed on them by the conveyor 2 (FIG. 1) by relative transmission in terms of the emission equipment of the incident beams and the detection equipment of the emergent beams. This ensures that the beams emitted successively from one cycle to the other strike the same eggs correctly. This is illustrated in FIG. 5, assuming that the beams pass through the egg OX1 and leave in zones that are very close to one another, inside a clearly circular zone Zs of small radial dimension around the summit of the egg. This condition is easy to fulfill, because the speed of transmission of the conveyor is weak compared to the speeds that can be attained in the field of optoelectronics.

For further clarification, if we consider a rhythm of transport that is typically 36,000 eggs per hour, each row containing 6 eggs, and a step between cells of 40 mm (in a more general sense this step is assumed to be between 30 and 50 mm), the time passing under the video camera 30 is about a 600 ms. Considering the technology available for applications of this type, an estimated time of approximately 150 ms is easily sufficient to conduct the capture of images by the video camera 30, and the analysis and processing of signals of images received by the calculator 6. During this period, the egg summit will have advanced by only 10 mm, or +/−5 mm with respect to the axis. Double or triple this range is possible, while maintaining sufficient precision, since what matters is not that the beam passes through the egg following its diameter, but that it strikes the lower sphere of the shell. This explains the possibility of submitting each row of cells to a third measurement cycle, and possibly a fourth, while increasing each time the duration of exposure and excluding those batches that, in the previous stage, called the first stage, revealed for the corresponding egg a condition that would cause a glare of the sensor in the following stage (second stage).

In particular, this possibility can advantageously be exploited to obtain an additional discrimination between the categories of egg within the range $G_3$ (FIG. 3: rotten eggs, eggs truly fertilized, and eggs containing false germs). This is followed by a third measurement cycle, different in duration from the two preceding. As further clarification, the respective durations of the three cycles could typically be as follows: 100 μs, 1 ms, and 4 ms.

The course of the two first cycles is very close to what has just been described for a process with only two cycles. By the end of the two first cycles, a discrimination has been possible between the vacant cells (first cycle) and between, on the one hand, the clear eggs and, on the other hand, the other categories of eggs (second cycle). The coordinates of the categories of eggs that have thus been discriminated on the completion of the second cycle are recorded by the calculator 6 in the memory facility.

During the third cycle, the cells capable of containing eggs in the range $G_3$ (FIG. 3) are illuminated by the third pulse. The mode of operation is similar to that of the second cycle. The calculator 6 puts out synchronized command signals to the video camera 30 and to the only diodes that are face to face with cells capable of containing eggs in a condition that leads to an attenuation of the range $G_3$. Accordingly it becomes possible to distinguish these categories of eggs. An interesting application consists in separately listing each of the categories that have thus been distinguished, which forms a tool for evaluating the quality of the fertilization on the part of the incubator, of the degree to which the crate grids are filled, and of the yield that can be expected from the hatching device.

After analysis of the content of the crate grids and of the recording of the coordinates of the various categories discriminated, two at most, namely clear eggs and fertilized eggs (either bearing a false germ, or rotten), or a greater number of categories (process with three cycles or more), these crate grids continue their path into the interior of the candling installation, carried by the conveyor 2 until the exit from this installation 1.

In practical terms, three principal possibilities exist (which can be cumulative):
 candling eggs according to just one class or several classes;
 simple sorting;
 compilation of statistics recorded in computerized databases, displayed and/or printed on listings.

It is generally desirable to mark at least the clear eggs, non-fertilized, which are to be set aside from the line leading to the hatchery for the production of chicks. In practice, after marking they are manually eliminated on leaving the installation, and then possibly recovered. They can serve as food or as a culture medium for producing vaccines.

To mark the eggs selectively according to the category to which they belong, with their coordinates recorded in databases, although this information is not sufficient, the plan is to correlate temporally the emergence of an egg of a given category, which is meant to be marked, with the moment it is marked, which is done as the eggs pass, row by row, through a predetermined zone at the exit of this installation, past a marking apparatus. To accomplish this, with reference once again to FIG. 1, there is a sensor 8, of any appropriate type, that detects the beginning of the passage of a new crate grid of eggs to be candled on the conveyor 2, for instance crate grid 4b, and at a connection at the exit 80 provides a synchronous pulse transmitted to the calculator 6. Preferably, in addition, the conveyor 2 comprises a displacement sensor 7 that, on a connection at the exit 70, delivers signals that permit the determination of the amplitude of the motion of this conveyor 2. These signals, correlated with the instant of emission of the synchronous pulse (connection 80), permit the calculation at any moment of the position reached by a given crate grid. In this manner it is possible, in particular, to know with precision the instant when a crate grid exits, for instance crate grid 4a: labeled 4'a when it leaves the installation 1 having run through the entire length of the portion of exit 21 of the conveyor 2.

Specifically, in the particular application described to illustrate the operation of the invention, the marking system 5 according to the invention is essentially made up of a number of inking apparatuses with devices that emit ink, or jets. These apparatuses are installed immovably above the conveyor. Corresponding to the quincunx arrangement of the cells of the crate grid, they are distributed in two subassemblies 52a and 52b, also in quincunx pattern between two parallel rows having as many inking apparatuses as there are cells in a row of the crate grid. In the perpendicular direction, the distance between the inking apparatuses is equal to one step of the distribution of the cells, and this applies on each of the two rows. In the longitudinal direction the space between the two rows is advantageously equal to a half-step as for the cells, allowing to control all the inking apparatuses at the same time However, another procedure is also possible when, for instance, it is desirable to separate the two subassemblies farther from one another by using at the same time a selected processing speed slower in the marking site than in the optical examination site.

Each inking apparatus is made up identically of an oil injector like those used elsewhere in the automotive industry to feed fuel to the cylinders of an internal combustion engine. The injectors are fed by a pump 50 by way of conduits made up, for instance, of flexible tubing of synthetic material, connected to the same belt circuit 500 that is fed from a reservoir of coloring liquid 51, by way of a conduit 510 in such a way as to maintain a constant liquid pressure in a buffer chamber for each injector. The coloring liquid is non-aqueous to avoid risks of rusting, and the various organs of the circuit, injectors and pumps, are constructed of steel alloys. A coloring product in an alcohol medium is preferably used. For a soluble coloring agent or an insoluble dispersed pigment, the alcohol has the dual advantage of being a readily available, economically priced organic solvent of being compatible with use in foods.

Control commands for the marking injectors are delivered by the calculator 6 in the form of pulses transmitted in two series of connections, 61a and 61b, and which, for each commanded marking injector, are addressed to an electromagnetic valve that determines the aperture of the jet releasing the coloring liquid, thus causing the emission of a pressurized spray of ink, 521a or 521b, that will mark the egg passing under the corresponding jet at this instant.

The marking system thus used according to the invention is particularly well adapted because the marks to be affixed on the eggs are simple ones, representing basic spots, and do not necessarily require preservation over time, and in addition the marking to be done does not concern all the objects passing through the installation but only some of them that have been identified in advance (particularly non-fertilized eggs). The requirements thus differ substantially from those prevailing, for instance, when eggs are to be marked for conveying precise information intended for consumers such as the laying date or similar details for which there is a need for sophisticated printing technologies to compose each character based on a matrix of pixels.

In terms of their mechanical installation, the inking apparatuses, with their respective jets, are immobile, advantageously fixed in place along the lines traversed by the objects on supporting rods perpendicular to the direction of motion, in an arrangement that aligns each of them with a corresponding object in the same row passing at their level. The inking liquid is permanently available there, under sufficient pressure so that the jet of ink reaches the object to be marked. For each individual jet, its release of ink is triggered by the opening of a valve at the moment when an object to be marked passes by. The absence of any contact between the inking apparatus itself and the object avoids the risk of any deterioration of the object so that in the case of eggs for instance, there is no danger of shell breakage.

In preferred embodiments of the marking system according to the invention, the inking apparatuses are installed on one or more rods forming supports that are arranged above the level traversed by the objects and aligned parallel to the rows of their distribution (perpendicular direction), so that the space between two injectors, or steps, is correlated to the step of the batches of objects, thus in particular to the step of the cells of the crate grids in the case of egg candling.

In a particular embodiment of the invention, the injectors of one rod are connected to their support by non-permanent hooking means allowing easy locking/unlocking and a regulation of the position of each injector along the support. Because of this characteristic, in which the injectors associated with a single row are installed on the support rod in positions that can be regulated laterally, the marking apparatus can easily accommodate various configurations of grids that contain the objects to be marked, whether eggs, fruits, or other items. Thus it is particularly easy to modify the distancing step between two adjacent injectors so that apparatuses can either maintain equal spacing among the batches in each row, or not.

In applications of the invention that are advantageous for situations where the crate grids have a quincunx arrangement of the cells, the marking apparatus, as described above, comprises two parallel supporting rods, so that the injectors of one rod are laterally unaligned with the injectors on the other rod in spatial correlation with the quincunx arrangement of the objects. In other embodiments of the invention that use variants, the injectors are mounted on their common support rod in such a way as to be able to move them laterally by a distance corresponding to the space between the objects from one row to the next and, on this basis, the lateral motion is controlled to correspond with the motion of the successive rows.

The marking command is given in coordination with the determination of the fertilized or non-fertilized condition of the eggs, depending on their lateral positions in a particular row of cells of the crate grid of on the time required for this row of cells to cover the distance separating their position during examination to determine their condition from their arrival in front of the printing jets that correspond to the cells receiving the eggs to be marked. In other words, in an installation that includes the marking system downstream from a candling system, the marking operations are performed at the same tempo as the visiometric examination operations, with a shift in time that is regulated by the speed of the conveyor that moves the egg crate grids along.

What is claimed is:

1. A method for analyzing objects received in individual cells arranged in successive transversal rows according to a continuous repetitive pattern along longitudinal lines on a conveyor belt that conducts the objects along the longitudinal direction through a visiometric examination site comprising receptors that are sensitive to emergent light beams transmitted from said objects, characterized in that examination of each row is conducted in at least first and second stages of successive actions while illuminating the transversal rows that are to be examined by different illumination doses and in the second stage illuminating only those transversal rows which, in the first stage, were not revealed as presenting a condition that would cause a glaring of the receptors during the second stage, wherein during said first stage, empty transversal rows of eggs are distinguished from those in which an egg is present, and coordinates of empty cells are determined and registered of said transversal rows in a current row in order to control illumination conditions during said second stage to avoid illuminating empty cells, and during said second stage, said objects are exposed to a light beam during a principal measurement cycle applied to each current successive row passing through said visiometric examination site only in examination sites where an egg is present.

2. The method according to claim 1, wherein the dose of illumination applied to each stage is regulated by varying an exposure time at a determined light intensity.

3. The method according to claim 1, wherein respective illumination doses of the two stages are selected to avoid glaring of the receptors that would disturb analysis, by operating in two different sensitivity scales.

4. An optoelectronic system for an installation that includes a conveyer for moving in a longitudinal direction comprising: egg receiving cells arranged according to a repetitive configuration of successive transversal rows along longitudinal lines, to move the cells through a visiometric examination site that comprises a light source, generating an incident illuminating beam from each of said eggs of each row successively under way in the visiometric examination site, and receptors for synchronized detection of emergent beams retransmitted by said eggs, characterized by directional means that synchronously control said light source and said means of synchronized detection to submit each row of cells to at least two cycles of successive measurements at different doses of illumination, namely:
  a first cycle, in the course of which all cells of a current row are illuminated by applying a weaker illumination dose, it is determined for each cell if it is an empty cell or not on the basis of a diminution of the light between incident beam and emergent beam, and coordinates of each empty cell whose presence is detected in this manner in said row are recorded in memory, and
  a second cycle in the course of which, by applying a stronger illumination dose, the only cells of the current row whose coordinates indicate the presence of an egg are illuminated, under conditions that are apt for automatically determining a condition of each of the said eggs on the basis of the consequences evoked for each on the light, between the incident and emergent beams.

5. An egg-candling installation comprising an optoelectronic system according to claim 4 to distinguish eggs according to a fertilized state on the basis of a decrease in luminous intensity caused by each egg between incident and emergent beams, as determined in the course of said second cycle.

6. The installation according to claim 5, further comprising an apparatus for marking said eggs, by imprinting spots whose shape and/or colors are determined and which are arranged in a predetermined position of said conveyor apparatus, and an apparatus for automatic analysis includes means to generate signals of selective command of this marking apparatus, in temporal relation with advance of crate grids on a conveyor apparatus and in spatial relation with coordinates of said eggs, which are to be marked in the crate grids presenting at least one of conditions that are to be identified.

7. An optoelectronic system for an egg-candling installation, comprising a conveyor for moving in longitudinal direction crates with egg receiving cells arranged according to a repetitive configuration of successive transversal rows along longitudinal lines, to make the cells pass through a visiometric examination site that comprises a light source, generating an incident beam for illuminating each of said eggs in each row successively in the visiometric examination site, and means of synchronized detection of the emergent beams retransmitted by said eggs, as well as means of analysis that automatically determines a fertilized or non-fertilized condition of said eggs, on the basis of a decrease caused by each egg in luminous intensity between incident and emergent beams, characterized in that said light source is made up of a rod comprising a number of light-emitting diodes aligned parallel to the rows of cells in said crates, and said means of synchronized detection comprising a number of photo detectors whose spatial configuration is correlated with that of the said light-emitting diodes, and further characterized in that means are provided for synchronously directing, during the passage of each successive row of cells in said visiometric examination site, first, a selective emission of incident beams by said light-emitting diodes and, second, a reception of corresponding emergent beams by said photo detectors in spatial relation with the emitting diodes, a direction being programmed to automatically ensure at least two measurement cycles involving different illumination durations for a single luminous power, namely, a shorter duration during a first stage and a longer duration during a second stage, and to illuminate during the said second stage only the cells for which said first stage has not revealed a risk of glaring the photodetectors during the second stage;
  wherein said first stage determines the presence or absence of an egg, and said illumination does not occur in said second stage if an egg is not present.

8. The system according to claim 7, wherein said light-emitting diodes emit in the infrared range.

9. The system according to claim 7, wherein said cells are arranged in a quincunx configuration, the number of said light-emitting diodes is double that of the cells of the said rows, and the diodes are controlled to emit alternately during passage from an even row to an odd row.

10. The system according to claim 7, wherein said eggs can present at least one condition in addition to said conditions of either fertilized or non-fertilized, and each additional condition is characterized by a decrease in the light crossing said eggs close to that associated with said fertilized condition, said cycles of light emission comprise a third cycle, distinct in duration from said first and second cycles, where said second cycle discriminates the non-fertilized eggs from fertilized eggs or those presenting an additional condition, and wherein this third cycle includes the emission of light illuminating cells whose coordinates indicate the presence of one of these conditions, of a third duration, longer than said first duration, and capable of discriminating said fertilized eggs from said eggs presenting a third condition, by detecting different decreases in the light crossing said eggs depending on their condition, and storage of the coordinates of the fertilized eggs and/or those of the third condition, where an illumination dose applied to each cycle is selected so as to avoid a risk of glaring the means of detection which are sensitive to emerging rays.

* * * * *